(12) United States Patent
Speier (10) Patent No.: US 10,677,872 B2
(45) Date of Patent: Jun. 9, 2020

(54) MAGNETIC RESONANCE APPARATUS AND METHOD FOR VASCULAR IMAGING

(71) Applicant: Siemens Healthcare GmbH, Erlangen (DE)

(72) Inventor: Peter Speier, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 155 days.

(21) Appl. No.: 15/984,894

(22) Filed: May 21, 2018

(65) Prior Publication Data

US 2018/0335497 A1 Nov. 22, 2018

(30) Foreign Application Priority Data

May 22, 2017 (EP) .................................... 17172146

(51) Int. Cl.
*G01R 33/563* (2006.01)
*G01R 33/56* (2006.01)
(Continued)

(52) U.S. Cl.
CPC .......... *G01R 33/5635* (2013.01); *A61B 5/055* (2013.01); *G01R 33/5607* (2013.01);
(Continued)

(58) Field of Classification Search
CPC .. G01R 33/5635; G01R 33/5607; A61B 5/055
See application file for complete search history.

(56) References Cited

U.S. PATENT DOCUMENTS 5,557,202 A 9/1996 Miyazaki et al.
5,627,468 A 5/1997 Kojima et al.
(Continued)

FOREIGN PATENT DOCUMENTS

CN 1618399 A 5/2005
CN 101564298 A 10/2009
(Continued)

OTHER PUBLICATIONS

Miyazaki, et. al.: "A Novel Saturation Transfer Contrast Method for 3D Time-of-Flight Magnetic Resonance Angiography: A Slice-Selective Off-Resonance Sinc Pulse (SORS) Technique", Magnetic Resonance in Medicine, vol. 32, pp. 52-59; (1994).

*Primary Examiner* — Dixomara Vargas
(74) *Attorney, Agent, or Firm* — Schiff Hardin LLP (57) ABSTRACT

In a magnetic resonance method and apparatus for time-of-flight vascular imaging, a magnetic field is applied to an imaging volume and an inflow volume, from which liquid enters into the imaging volume, of an examination person. The imaging volume is excited by an RF pulse, which fulfills a magnetization transfer function and a fat saturation function, while the magnetic field is being applied. The RF pulse has a frequency distribution whose frequencies are higher than the center frequency of water in the imaging volume, and that includes the fat frequency in the imaging volume. The magnetic field has a field distribution with an apex with essentially no spatial gradient in the imaging volume and having a higher spatial gradient in the inflow volume, so that the center frequency of water in the inflow volume is shifted in the direction of lower frequencies and is no longer affected by the RF pulse.

16 Claims, 5 Drawing Sheets

(51) Int. Cl.
  *A61B 5/055* (2006.01)
  *G01R 33/3875* (2006.01)
  *A61B 5/02* (2006.01)
  *G01R 33/44* (2006.01)

(52) U.S. Cl.
  CPC ...... *A61B 5/02007* (2013.01); *G01R 33/3875* (2013.01); *G01R 33/446* (2013.01); *G01R 33/5601* (2013.01); *G01R 33/5605* (2013.01)

(56) References Cited

U.S. PATENT DOCUMENTS

| | | | | |
|---|---|---|---|---|
| 8,131,338 | B2* | 3/2012 | Kassai | A61B 5/055 600/407 |
| 9,194,923 | B2* | 11/2015 | Yokosawa | A61B 5/055 |
| 9,606,211 | B2* | 3/2017 | Chung | G01R 33/56563 |
| 9,678,187 | B2* | 6/2017 | Shirai | G01R 33/56518 |
| 2005/0110489 | A1 | 5/2005 | Miyoshi | |
| 2009/0005670 | A1 | 1/2009 | Ichinose et al. | |
| 2009/0185981 | A1* | 7/2009 | Karczmar | A61B 5/055 424/9.3 |
| 2009/0267604 | A1 | 10/2009 | Umeda | |
| 2011/0251477 | A1 | 10/2011 | Schmitt | |
| 2014/0070805 | A1 | 3/2014 | Van Der Meulen et al. | |
| 2015/0272453 | A1 | 10/2015 | Heberlein et al. | |
| 2016/0154081 | A1* | 6/2016 | Chung | G01R 33/56563 324/309 |
| 2016/0266223 | A1 | 9/2016 | Bi et al. | |
| 2016/0291111 | A1 | 10/2016 | Pfeuffer et al. | |
| 2018/0335497 | A1 | 11/2018 | Speier | |

FOREIGN PATENT DOCUMENTS

| | | |
|---|---|---|
| CN | 103649765 A | 3/2014 |
| CN | 102217935 B | 2/2015 |
| CN | 104605852 A | 5/2015 |
| CN | 108931749 A | 12/2018 |
| JP | 2005152534 A | 6/2005 |

* cited by examiner

MAGNETIC RESONANCE APPARATUS AND METHOD FOR VASCULAR IMAGING

BACKGROUND OF THE INVENTION

Field of the Invention

The present invention concerns a method of vascular imaging with the use of a magnetic resonance (MR) system (i.e., the scanner thereof) based on the Time-of-Flight (TOF) technique. Furthermore, the invention concerns an associated MR system, and a non-transitory electronically readable data storage medium, that implement such a method.

Description of the Prior Art

One category of MR imaging methods, in particular perfusion and angiography scans using the TOF technique, as well as some 2D-cardiac imaging methods, uses an inflow-based contrast. With the latter, the inflow intensifies only the existing contrast of the vessel walls and therefore simplifies their visualization, whereas perfusion and angiography scans are based solely on inflow-based contrast. In the case where quantitative inflow information is to be extracted, such as in perfusion scans, a differential imaging method is applied to eliminate the background signal; a subtraction of two data sets having different inflow magnetization preparations is carried out. However, this approach doubles the scanning time and requires and also requires the two data sets to be brought into registration with each other. Therefore, this step is skipped in cases in which quantitative information is not required, for example with imaging of the vascular geometry. Instead, the background signal is suppressed as far as possible with the use of appropriate MR methods.

MR imaging based on the TOF technique is a non-invasive imaging method for visualizing the vessel structure of an examination object, which is based on the inflow of "fresh", not-previously saturated spins into an imaging volume. The fixed magnetization, i.e., the fixed spins of the imaging plane, are saturated by repeated excitation in a short interval. The signal of this magnetization is largely suppressed, while the not-previously saturated magnetization, which results due to the blood flow into the imaging plane during the recording, has a high signal component.

For MR imaging based on the TOF technique of the head vessel system, the methods described below are known for suppressing the background signals caused by brain tissue, spinal fluid and fat.

A first known method for suppressing the background signals is the application of large flip angles during image acquisition in order to suppress tissue having long T1-times, in particular liquids. The flip angle is limited by the fact that it reduces the signal with each pulse, therefore it limits the distance over which inflowing spins can be observed in the imaging volume, in other words, the slice thickness of the imaging volume. Typically, flip angles in the range of 15 degrees/24 ms allow good background signal suppression with slice thicknesses of up 2 cm.

A further known method for suppressing background signals is the opposed-phase imaging method. Here, the echo time (TE) is chosen such that fat and water are not in phase (dephased), for example roughly 7 ms at 1.5 T and 3.4 ms at 3 T. As a result, signals of voxels, which contain a water-fat mixture, are reduced. However, voxels having pure fat are always still brightly visible and impair the vessel visibility in these regions, or in general in non-selective maximum intensity projections (MIP). In particular, at 1.5 T this condition lengthens the echo time, resulting in a T2*-based signal loss and a lengthening of the acquisition time. To stabilize the signal for echo times of this kind, flow compensation gradients must be applied. Dephasing due to a laminar, straight flow is compensated, but not dephasing due to a turbulent flow or a flow along a curve. It would therefore be advantageous to minimize the echo time, for example by using ultrashort Echo Time (UTE) techniques, and to suppress the background signal of fat using a different method.

A further known method for suppressing background signals is saturation by magnetization transfer (MT), by the use of an MT pulse. In the process immobile protons in macromolecules having a broadened resonance frequency are saturated by strong RF pulses having frequencies in ranges, of which 500 Hz to 2000 Hz lie next to the frequency of water. These protons couple with the observable highly mobile water protons, so that saturation of the immobile protons also leads to saturation of the observed signal. However, observable fat protons are not coupled as strongly to the immobile protons and for this reason the fat signal cannot be suppressed by this method. Saturation can be intensified by increasing the irradiated RF energy, limited by Specific Absorption Rate (SAR) limit values, and by minimizing the distance of the frequency from the resonance frequency, limited by the saturation of the blood. Since the MT pulse is non-selective, the saturation along the supplying vessels, for example the carotids, must be taken into account in addition to the saturation of the blood within the imaging volume.

From U.S. Pat. No. 5,627,468 A and the article "A Noise Saturation Transfer Method for 3D Time-of-Flight Magnetic Resonance Angiography: A Slice Selective Off-Resonance Sinc Pulse (SORS) Technique" by Miyazaki et al., Magnetic Resonance in Medicine, Vol. 32, pp. 52-59 (1994), a further method of suppressing background signals is known in which a Slice-Selective-Off-Resonance-Sinc (SORS) pulse with a linear gradient field along the z-axis is used. The method includes a first sequence with the application of the SORS pulse and a second sequence for recording MR scan data. The frequency of the SORS pulse is chosen such that the water frequency above the imaging volume is met, so that no water excitation, but only an MT effect, occurs within the imaging volume. In addition, venous blood above the imaging volume is saturated thereby, so that the SORS pulse is simultaneously used to block signals from venous blood. Due to the linear gradient field, the distance between the pulse frequency band and the water frequency increases below the imaging volume linearly with the distance from the imaging volume, so that the saturation of the inflowing blood is reduced due to an inadequate frequency band limitation of the SORS pulse. By a suitable choice of the polarity of the SORS pulse, the method can also be used for a fat saturation, although, due to the linear gradient along the slice selection direction, the fat saturation is typically inhomogeneous with method parameters differing slightly from the optimum and with slight B0 inhomogeneities.

Furthermore, a technique known as frequency-selective fat saturation is known for suppressing background signals. With a frequency-selective, spatially non-selective RF pulse, the fat magnetization is excited in the imaging volume without exciting the water magnetization in the imaging volume. The transverse magnetization of the excited fat magnetization is also extinguished by gradient spoiling and the water signal can therefore be measured separately. However, this method is unreliable since it saturates the blood in the supplying vessels, and some blood vessels in the imaging volume cannot be resolved as a result. This undesirable saturation of the blood in the supplying vessels is caused by inhomogeneities in the B0 magnetic field, in particular in the neck area and the upper chest of an examination person, wherein, in particular, the water frequency is shifted by the inhomogeneities to the nominal fat frequency, in other words, in the direction of the higher frequencies.

Due to the described drawbacks of the conventional methods of suppressing background signals, manual post-processing of the MR image must often also be carried out by cutting out the percutaneous fat before generating maximum intensity projections (MIP), and this leads to increased time and staff expenditure, and therewith increased examination costs.

MR methods in which, inter alia, background signals are also suppressed, are disclosed for example in DE 10 2015 205 694 B3, US 20160266223 A1, and US 20150272453 A1.

SUMMARY OF THE INVENTION

There is therefore a need for an improved method of suppressing background signals in MR imaging based on the TOF technique, which suppresses background signals of brain tissue, spinal fluid and fat in a highly reliable manner, which provides a good contrast of MR images and good detectability of in particular small vessels, and which consequently enables efficient and inexpensive MR imaging without the need for manual post-processing of the MR images.

This object is achieved by the method, MR apparatus and storage medium of the invention.

According to a first aspect of the invention, a method for vascular imaging with the use of an MR apparatus has a first step wherein a magnetic field is applied to an imaging volume and an inflow volume, from which liquid enters into the imaging volume, of an examination person. In a further step, the imaging volume is excited by an RF pulse, which fulfills a magnetization transfer function and a fat saturation function, while the magnetic field is being applied. The RF pulse, which fulfills a magnetization transfer function and a fat saturation function, can be exactly one RF pulse. The imaging volume can also be excited by an RF preparation block. An RF preparation block can be one or more RF pulse(s), which fulfill a fat saturation function, a magnetization transfer function and a TSAT function. In an additional step, MR signals from the imaging volume are measured in order to visualize vessels. The RF pulse has a frequency distribution whose frequencies are essentially higher than the center frequency of the water in the imaging volume, in other words, located on the side of the fat frequency, and which include the fat frequency in the imaging volume. The magnetic field also has a magnetic field distribution, which is approximated by a function that is designed to have an apex with essentially no spatial gradient in the imaging volume, and to have a higher spatial gradient in the inflow volume. The function, which the magnetic field distribution approximates, can be non-linear. The function, which the magnetic field distribution approximates, can also have a saddle point of an antisymmetric gradient, for example a z3 shim, instead of the apex of a symmetrical gradient, for example a z2 shim.

The field distribution is designed so that the center frequency of the water in the inflow volume is shifted in the direction of lower frequencies, so that it is no longer affected by the RF pulse. In particular, the field distribution of the magnetic field can have an essentially constant field strength within the imaging volume. In particular, the field fluctuations of the magnetic field within the imaging volume can be smaller than the frequency spacing between the fat frequency and the water frequency, enabling a homogeneous fat saturation. A longitudinal direction can also be defined so as to run in the direction from foot to head of an examination person, wherein the longitudinal direction runs through the center of the imaging volume and the center of the inflow volume, and wherein it is also conventionally designated as the z-direction. In the inflow volume, the field distribution of the magnetic field has a higher field strength gradient in the longitudinal direction compared to the imaging volume. In other words, the field strength of the magnetic field increases non-linearly in the z-direction and is approximated by a mathematical function of at least the second order. With respect to the B0 field, the magnetic field has a polarity, which reduces the field strength of the B0 field outside of the imaging volume, at least in the direction from which the blood flows in, i.e., at least in the inflow volume. As a result, the center frequency of the water is shifted in the direction away from the fat frequency, in particular toward lower frequencies, and furthermore, is shifted non-linearly with increasing distance in the longitudinal direction toward lower frequencies.

With the inventive method, in the case of vascular imaging with the use of an MR apparatus based on the TOF technique, background signals of brain tissue, spinal fluid and fat are reliably suppressed and a higher contrast and better detectability of small vessels in the vicinity of the cranium and the eye sockets is provided in the resulting MR images, compared to conventional methods for suppressing background signals. Furthermore, with the inventive method, the application of opposed-phase imaging methods for suppressing background signals can be omitted, so that the TE can advantageously be minimized in the existing scanning protocol, and, particularly advantageously, much quicker Ultrashort Echo Time (UTE) MR imaging with high contrast and without signal gaps due to turbulent flows is enabled. Furthermore, with the inventive method, the need for manual post-processing of the MR images in order to manually remove percutaneous fat is omitted. In particular, the vessel visibility of Inline SAG and COR MIPs is improved, and this in turn reduces the need for manual "cranial releasing", as is typically carried out in a hospital's daily routine. As a result, faster and more efficient MR imaging of vascular visualization is enabled with the use of an MR apparatus, which has a lower time and staff expenditure for an examination, and thereby reduced examination costs compared to conventional methods of vascular imaging with the use of an MR apparatus.

The imaging volume and the inflow volume can be slice-like, wherein a longitudinal axis can be oriented perpendicularly to the imaging volume and the inflow volume, and wherein along the longitudinal axis, a slice thickness of the inflow volume can be equal to a multiple of a slice thickness of the imaging volume.

Due to the slice-like form and the smaller slice thickness of the imaging volume compared to the inflow volume, the contrast of the MR image is increased further in vascular imaging.

The apex of the function can essentially have the same thickness as the slice thickness of the imaging volume, so that the background signals due to inhomogeneities in the inflow volume are reliably reduced.

The steps of the method can be carried out for at least one further imaging volume and at least one further inflow volume. The method can also comprise an adjustment of the magnetic field distribution to the at least one further imaging volume and the at least one further inflow volume in such a way that the adjusted magnetic field distribution in the at least one further imaging volume has the apex and in the at least one further inflow volume has the higher spatial gradient.

The reliability and the contrast of the MR imaging is increased further by the implementation of the method for a plurality of imaging volumes and inflow volumes.

The adjustment of the magnetic field distribution can include linear spatial shifting of the magnetic field distribution, so that the adjustment of the magnetic field can be carried out quickly and efficiently.

The adjustment of the magnetic field distribution can include a change to linear components of the magnetic field distribution, further increasing the efficiency of the adjustment.

The multiple imaging volumes can at least partially spatially overlap. The method is less error-prone and suppression of the background signals is more reliable due to the spatial overlapping of the number of imaging volumes.

The method can also include generating the RF pulse by overlaying a first RF pulse and a second RF pulse. Generating an RF pulse by overlaying a first RF pulse and a second RF pulse enables a more exact adjustment of the RF pulse to a plurality of functions, for instance a magnetization transfer function and a fat saturation function, and therewith more efficient suppression of the background signals.

The first RF pulse can have a first flip angle and the second RF pulse a second flip angle different from the first flip angle, so that the RF pulse can be adjusted for the excitation of different tissue, so that it can fulfill for instance a magnetization transfer function and a fat saturation function.

The first RF pulse can preferably has a flip angle of 20 to 180 degrees, particularly preferably 90 degrees, and a frequency essentially equal to the fat frequency in the imaging volume. These values are particularly advantageous for the fat saturation function of the RF pulse. If measurement of the MR signals in the Steady State is carried out exactly in the middle between the RF pulses for fat saturation, an inversion, in other words, 180 degrees, is optimum for complete extinguishing of the fat signal, but typically smaller flip angles limited by SAR are used. With RF pulse intervals <<T1 of fat, as in the above-described method, a flip angle <<90 degrees can also achieve good fat saturation.

A number of measurements of MR signals from the imaging volume can be carried out per RF pulse, so that the scanning time for recording an MR image is reduced.

The number of measurements can be carried out at regular time intervals, so that the image quality of the MR images is improved.

The number of measurements can be carried out in measurement groups with time intervals between the individual measurements, wherein an excitation by an RF pulse or an RF preparation block can be carried out between the measurement groups, and wherein the mean time interval between the scans can be less than a predetermined threshold value. An RF preparation block can comprise one or more RF pulse(s), which fulfill a fat saturation function, a magnetization transfer function and a TSAT function. The image quality of the MR images is improved further by the temporal grouping of the individual measurements into measurement groups with an RF pulse played between the measurement groups in that the RF pulse can have a well-defined frequency profile. Furthermore, the SAR exposure for the examination object is reduced.

The invention also encompasses an MR apparatus for vascular imaging having an MR data acquisition scanner operated by a control computer, and a memory, wherein the memory stores control information (code) that can be executed by the control computer so that, when executing control information in the control computer, the method as described above is implemented.

The MR apparatus of this kind for vascular imaging according to the invention achieves technical effects comparable to the technical effects that were described above for the method according to the invention.

The present invention also encompasses a non-transitory, computer-readable data storage medium encoded with programming instructions (program code) that, when the storage medium is loaded into a computer or computer system of a magnetic resonance imaging apparatus, cause the computer or computer system to operate the magnetic resonance imaging apparatus in order to implement any or all embodiments of the method according to the invention, as described above.

The features described above and the features that are described below can be used not just in the corresponding explicitly described combinations but also in further combinations or alone, without departing from the scope of the present invention.

DESCRIPTION OF THE PREFERRED EMBODIMENTS

Figure 2:
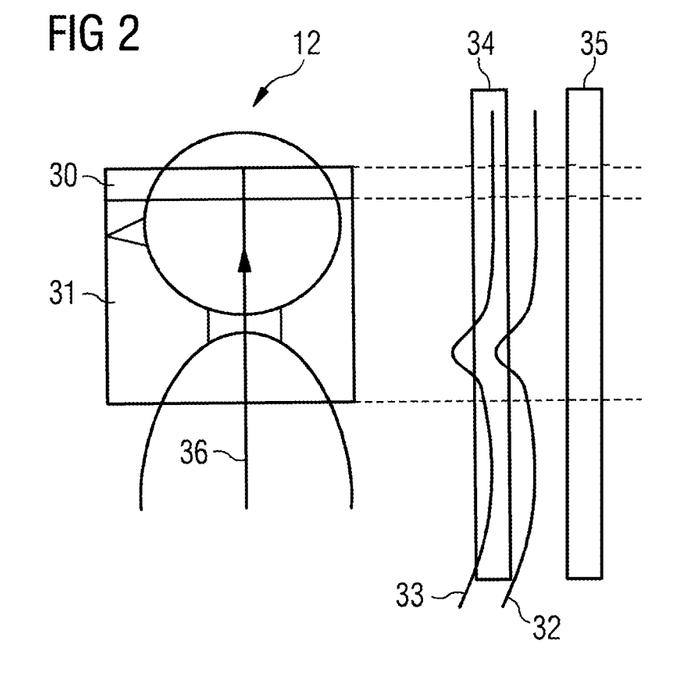
FIG. 2 schematically illustrates an examination person with associated frequency characteristics without an inventively applied magnetic field.

The present invention relates to a method of vascular imaging with the use of an MR system. With reference to FIG. 2, in a vascular imaging based on the TOF technique, a fixed magnetization, in particular of brain tissue, spinal fluid and fat, which generate an undesirable background signal in an imaging volume 30, is saturated by an RF pulse 40 with simultaneously applied inventive magnetic field. The RF pulse 40 and the applied magnetic field are designed so as to suppress the background signals without exciting the spins of the vessel fluid flowing into the imaging volume.

Figure 1:
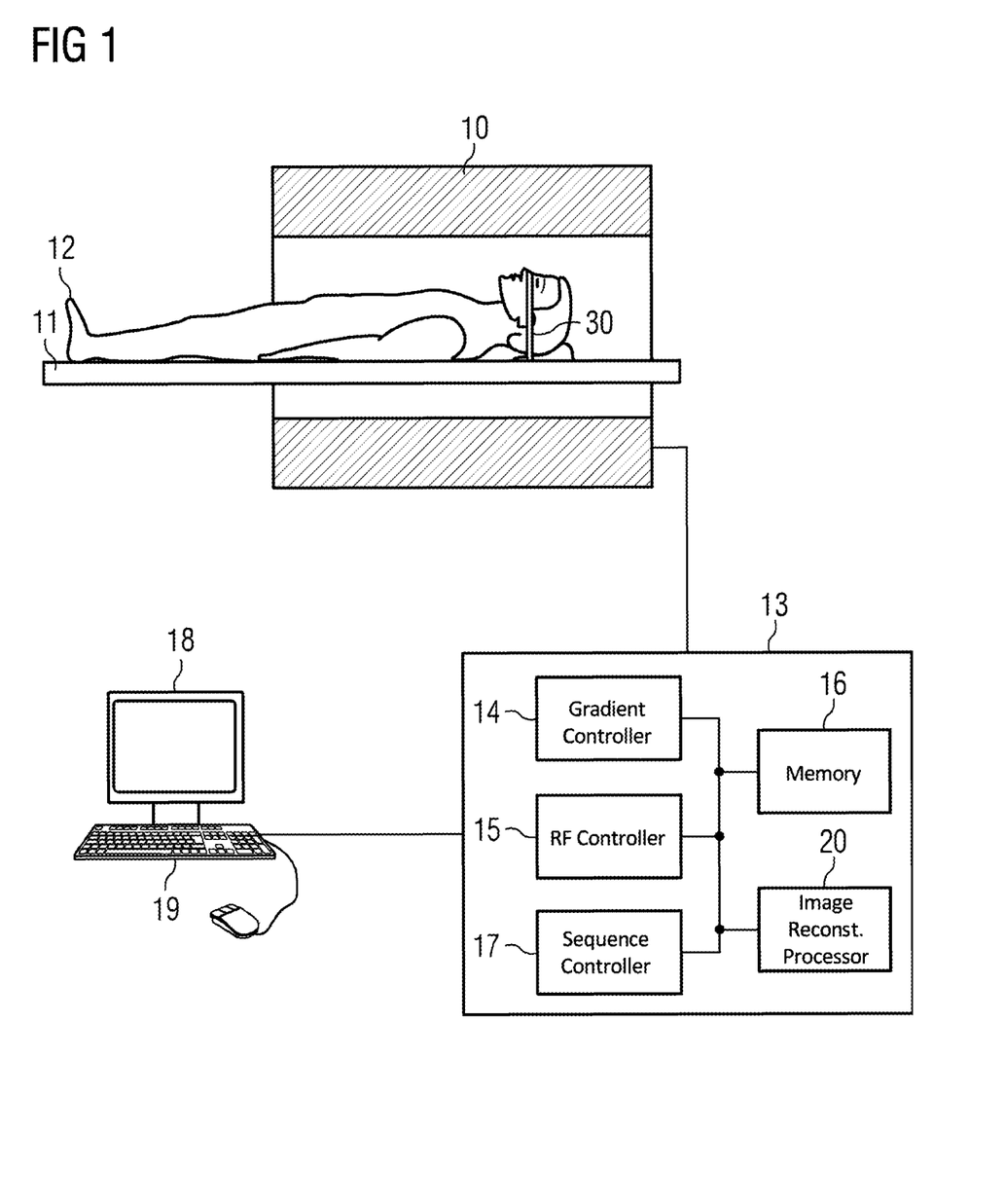
FIG. 1 schematically shows an MR apparatus with which the method of vascular imaging can be inventively carried out.

FIG. 1 schematically shows an MR apparatus with which such a method of vascular imaging can be inventively carried out.

An examination person 12, or, more generally, an examination object, is moved into the tunnel of the an MR data acquisition scanner 10 that has a magnet that generates a basic field B0, with the examination person 12 on a bed 11 being moved into the center of the scanner 10 in order to record spatially encoded magnetic resonance signals from an examination, volume or region. By radiating radio-frequency pulse sequences and switching magnetic field gradients, certain nuclear spins in the examination person 12 are given a magnetization that causes those nuclear spins to be deflected from the steady state produced by the basic field B0, by an amount known as a flip angle. As those excited nuclear spins relax and return to the steady state, they emit RF signals (MR signals) that are detected by the same antenna from which the excitation pulses were radiated, or a different antenna. The acquired MR signals are entered into a memory organized as k-space, as raw MR data (k-space data). The raw MR data are transformed in a known manner into image data. The general manner of operation for creating MR images and detection of the magnetic resonance signals are known to those skilled in the art, so that a more detailed description is not necessary herein.

The magnetic resonance apparatus also has an MR control computer 13 that controls the scanner 10. The central control computer 13 is designed such that the method described below is carried out automatically, and has a gradient controller 14 that controls and switches the magnetic field gradients and an RF controller 15 that controls and radiates the RF pulses for deflecting the nuclear spins from the steady state. For example, the imaging sequences necessary for recording the MR images, as well as all programs that are needed to operate the MR apparatus, are stored in a memory 16. A sequence controller 17 controls the acquisition of raw MR data and therewith controls, as a function of the chosen imaging sequences, the sequence of the magnetic field gradients and RF pulses and the receiving intervals of MR signals. The sequence controller 17 thereby also controls the gradient controller 14 and the RF controller 15. MR images can be reconstructed from the acquired raw data in an image reconstruction processor 20, and these images can be displayed on a display 18. An operator can operate the MR system via an input unit 19. The memory 16 can have imaging sequences and program modules stored therein to implement the inventive method. The RF controller 15 is designed to improve suppression of background signals with vascular imaging based on the Time-of-Flight (TOF) technique, as will be illustrated below in detail. In particular, the memory 16 stores for this purpose control information that can be executed by the control computer 13. Furthermore, the sequence controller 17 is designed to carry out the method of vascular imaging described below.

According to the invention, the MR apparatus of FIG. 1 is designed so that, during implementation of the control information in the MR control computer 13, it applies a magnetic field to an imaging volume 30 and to an inflow volume 31, from which liquid enters into the imaging volume 30, of an examination person 12, as shown in FIG. 2. Furthermore, the imaging volume 30 is excited by an RF pulse 40, which fulfills a magnetization transfer function and a fat saturation function, while the magnetic field is being applied. Furthermore, MR signals from the imaging volume 30 are measured to visualize vessels, which are in the imaging volume. The RF pulse 40 has a frequency distribution whose frequencies are essentially higher than the center frequency of the water 32 in the imaging volume 30, and which comprises the fat frequency 33 in the imaging volume 30. Furthermore, a field distribution of the magnetic field is approximated by a function, which is designed in such a way that it has an apex with essentially no spatial gradient in the imaging volume 30 and has a higher spatial gradient in the inflow volume 31.

FIG. 2 schematically illustrates an examination person with associated frequency characteristics of the water frequency and fat frequency without inventive applied magnetic field.

An examination person 12 has an imaging volume 30 and an inflow volume 31. A blood vessel 36 is contained in the imaging volume 30 and the inflow volume 31, so that blood flows out of the inflow volume 31 into the imaging volume.

The imaging volume 30 and the inflow volume 31 have a slice-like form in this exemplary embodiment. Furthermore, a longitudinal axis is oriented perpendicularly to the imaging volume 30 and the inflow volume 31, and wherein along the longitudinal axis, a slice thickness of the inflow volume (31) is equal to a multiple of a slice thickness of the imaging volume (30). The blood vessel 36 likewise runs essentially along the longitudinal axis.

Under the influence of the B0 field the examination person 12 has a water frequency 32, which corresponds to the liquid in the vessel, in particular the blood in the blood vessel. The water frequency 32 has a spatial characteristic in the z-direction, or head-foot direction of the examination person 12. The water frequency 32 runs constantly in the region of the imaging volume 30, whereas due to inhomogeneities of the gradient field within the inflow volume 31, the water frequency is shifted in a section of the inflow volume 31. In this section the water frequency 32 runs in the fat saturation band 34. Furthermore, the examination person 12 under the influence of the B0 field has a fat frequency 33, which corresponds to fat accumulations, fatty deposits or other fatty tissue of the examination person 12 in the imaging volume 30. In the region of the imaging volume 30 the fat frequency 33 runs within a fat saturation band 34. Within the inflow volume 31 the fat frequency 33 has a corresponding frequency shift like the water frequency 32. A magnetization transfer band 35 runs next to the water frequency 32 on the side, which is remote from the fat frequency, or in other words, next to the water frequency 32 in the direction of lower frequencies, without overlapping the water frequency 32. The B0 field decreases in the edge regions of the examination person, so that the water frequency 32 and the fat frequency 32 also decrease. This means that when a saturation pulse with the band 34 is used, parts of the inflowing blood would also be saturated, and this is undesirable.

Figure 3:
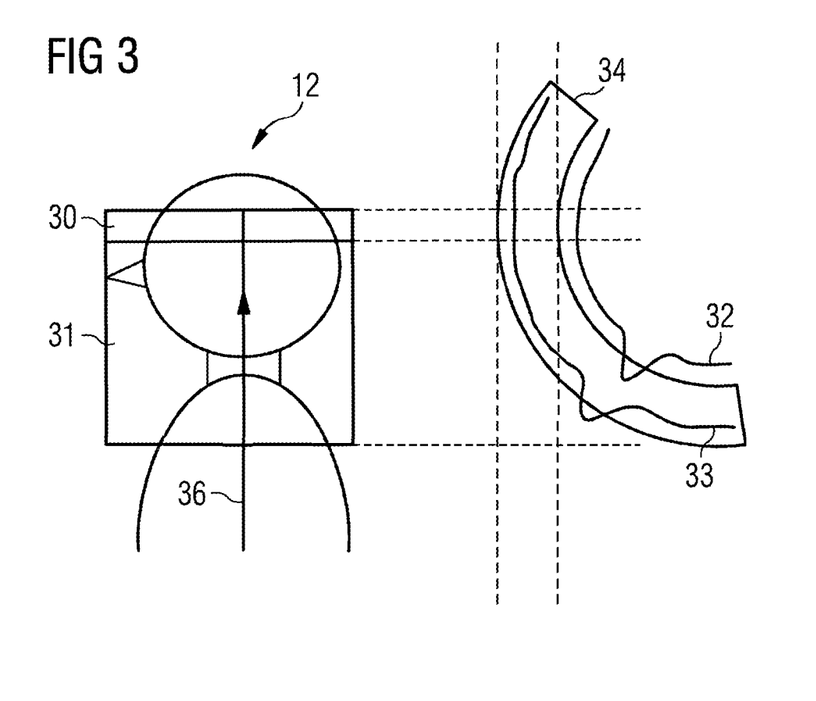
FIG. 3 schematically illustrates the examination person of FIG. 2 with associated frequency characteristics with an applied magnetic field of the invention.

FIG. 3 schematically illustrates the examination person of FIG. 2 with the associated frequency characteristics with an applied magnetic field according to an exemplary embodiment of the invention.

While the magnetic field is being applied, the resonance frequencies in the sphere of influence of the magnetic field, and in particular the resonance frequencies in the inflow volume 31, are shifted. According to the invention, the magnetic field is designed in such a way that the shift in the resonance frequencies in the inflow volume 31 increases with a, compared to the imaging volume 30, higher gradient, in particular non-linearly at a distance in the z-direction from the imaging volume 30.

The water frequency 32 in the inflow volume 31 is shifted in the direction away from the fat saturation band 34 in such a way that a non-selectively irradiated fat saturation pulse, which has a frequency distribution that corresponds to the fat saturation band 34 in the region of the imaging volume 30, does not comprise the water frequency 32 in the region of the inflow volume 31. As a result, blood, which is located in the blood vessel 36 in the inflow volume 31 and which flows into the imaging volume 30, is not excited.

In an exemplary embodiment, in which the blood vessel 36 is located in vicinity of the isocenter of the imaging volume 30, the magnetic field can be applied by way of an adjustment of the z2 shim, wherein the remaining shims of the second order must consequently also be adjusted.

In a further exemplary embodiment, a simple shim algorithm can comprise the following steps: optimizing the B0 homogeneity in the imaging volume 30 with the boundary condition of keeping the z2 shim at a fixed value, for example with the Tune-Up value plus 1500 μT/M^2.

In another exemplary embodiment, the steps of the method are carried out for at least one further imaging volume and at least one further inflow volume. Condition for a fat saturation over the entire imaging volume limits the value of the z2 offset. This limit scales with an extension of the imaging volume 30 in the z-direction. The TOF technique is always carried out using the Multiple Overlapping Transverse Slab Acquisition (MOTSA) technique. For example, a transverse examination volume with 10 cm slice thickness is covered by 6 overlapping imaging volumes 30 with 2 cm slice thickness. The imaging volumes 30 are scanned sequentially. The magnetic field therefore can be individually optimized and adjusted for each imaging volume 30. In one exemplary embodiment the quadratic field distribution is shifted along the z-axis. With oblique imaging volumes (typically T>C), the z2 value must be reduced so it matches the thickness of the imaging volume when this is projected onto the z-axis. In a further exemplary embodiment, the parabolic direction must be inclined using the other shim channels of the second order.

The magnetic field distribution is therefore adjusted to the at least one further imaging volume and the at least one further inflow volume such that the adjusted magnetic field distribution in the at least one further imaging volume has the apex and in the at least one further inflow volume has the higher spatial gradient.

In another exemplary embodiment, multiple measurements (data acquisitions) are carried out per RF pulse 40. The RF pulses 40 should not lengthen the image recording duration. Therefore, a plurality of read outs is carried out per RF pulse, wherein the mean time interval between the read outs is kept constant in order to retain the TOF contrast, for example instead of one readout per repetition time TR=24 ms, two readouts could also be carried out in 48 ms or three readouts in 72 ms. The image quality is independent of the positioning of the readouts in the TR, they can be played equidistantly or without pause, so that a longer pause per TR is permitted, which is long enough to play a long MT and fat saturation pulse, which has a well-defined frequency profile and a low SAR.

In one exemplary embodiment, TSAT pulses and MT pulses are played alternately. In a further exemplary embodiment, TSAT pulses and MT pulses are played alternately with varying repetition time TR. In a further exemplary embodiment, at least one TSAT pulse and at least one MT pulse are played in a repetition time TR.

Figure 4A:
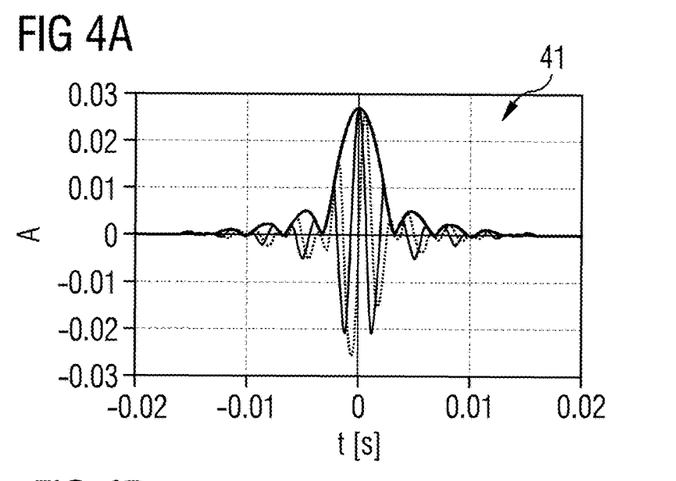
FIGS. 4A, 4B, and 4C show a first RF pulse for generating the RF pulse according to one exemplary embodiment of the invention.
Figure 4B:
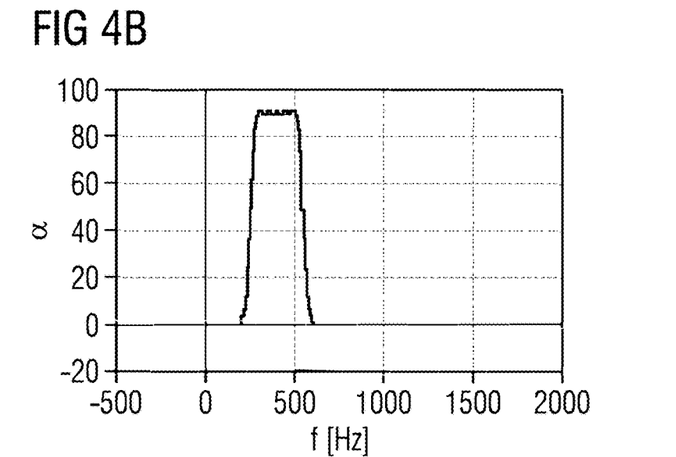
Figure 4C:
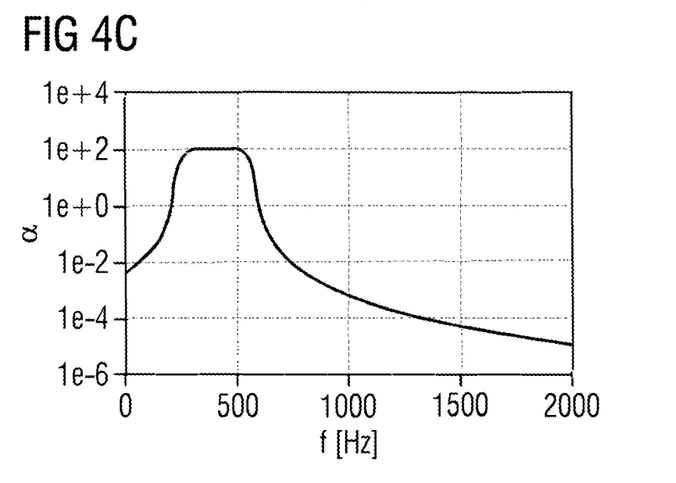

FIGS. 4A, 4B and 4C show a first RF pulse for generating the RF pulse according to an exemplary embodiment of the invention.

FIG. 4A shows a graph of a complex amplitude A of a first RF pulse 41 over time.

FIG. 4B shows the flip angle a of the first RF pulse 41 in the frequency domain.

FIG. 4C shows the flip angle a of the first RF pulse 41 in the frequency domain in a logarithmic graph.

The first RF pulse 41 preferably has a flip angle of 20 to 90 degrees, particularly preferably 90 degrees, and a frequency essentially equal to the fat frequency 33 in the imaging volume 30.

Figure 5A:
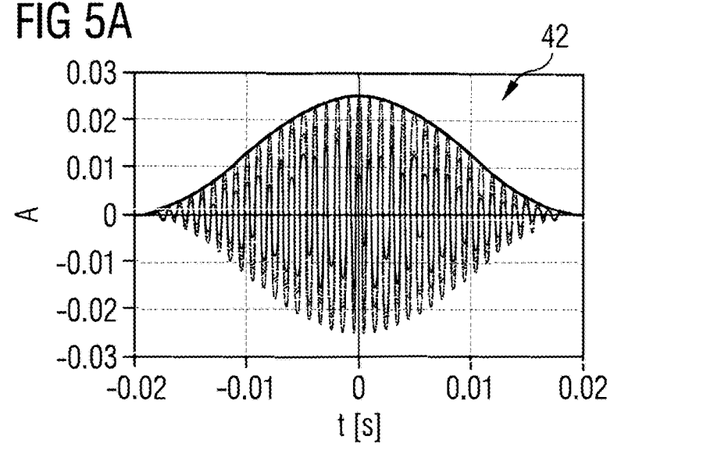
FIGS. 5A, 5B and 5C show a second RF pulse for generating the RF pulse according to an exemplary embodiment of the invention.
Figure 5B:
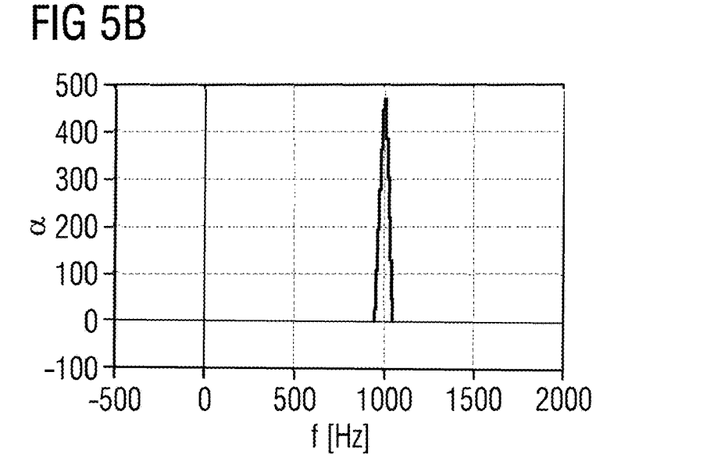
Figure 5C:
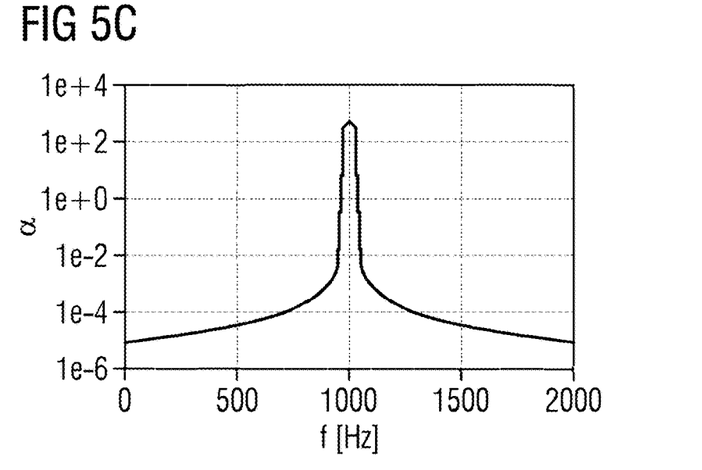

FIGS. 5A, 5B, and 5C show a second RF pulse for generating the RF pulse according to another exemplary embodiment of the invention.

FIG. 5A shows a graph of a complex amplitude A of a second RF pulse 42 over time.

FIG. 5B shows the flip angle a of the second RF pulse 42 in the frequency domain.

FIG. 5C shows the flip angle a of the second RF pulse 42 in the frequency domain in a logarithmic graph.

The second RF pulse 42 preferably has a flip angle of a few hundred degrees, more preferably 500 to 600 degrees, and a frequency of 1 kHz to 1.5 kHz, particularly preferably 1.5 kHz.

Figure 6:
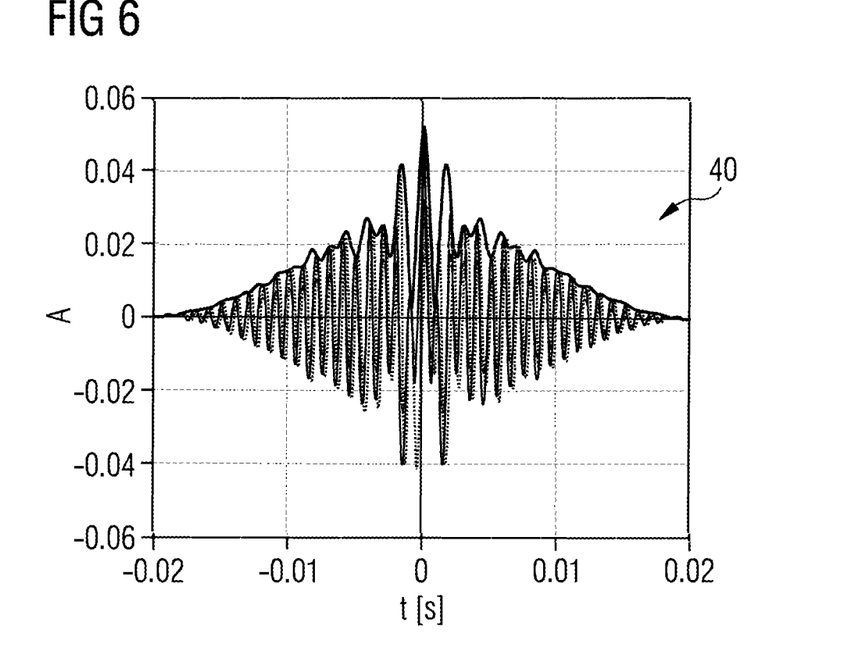
FIG. 6 shows an RF pulse according to an exemplary embodiment of the invention.

FIG. 6 shows an RF pulse 40 according to an exemplary embodiment of the invention.

The RF pulse 40 was generated by overlaying the first RF pulse 41, as shown in FIGS. 4A-4C, and the second RF pulse 42, as shown in FIGS. 5A-5C.

In an exemplary embodiment, the RF pulse is optimized for fat saturation and MT. MT requires a much higher flip angle than fat saturation. For effective fat saturation, a flip angle of no more than 90 degrees per TR (50 ms) is already sufficient, whereas the MT flip angle should be as high as possible. In some exemplary embodiments, the MT flip angle is 6-10 times as high as the flip angle for fat saturation. Undesirable saturation of the water frequency increases with the flip angle and reduces with increasing distance from the water frequency and SAR-intensive pulse profile optimizations. Since the MT effect depends to only a slight extent on the distance from the water frequency, the RF pulse can be optimized in such that it provides the flip angle, which is necessary for fat saturation, and provides the remaining flip angle in the case of a greater frequency spacing next to the water frequency, for example at 1.5 kHz. This is achieved by overlaying the pulse envelopes of the first RF pulse 41 and the second RF pulse 42, for example RF pulses with 2ex20: 90 degrees at the fat saturation frequency and 500 degrees at 1 kHz.

In an exemplary embodiment, the RF pulse 40 preferably has a uniform flip angle of 90 degrees at approximately 400 Hz next to the water frequency 32, and a flip angle of 500 degrees in the vicinity of 1 kHz next to the water frequency 32, wherein the flip angle is negligible at the water frequency, or less than 1 degree. The RF pulse 40 is on the side of the water frequency 32 at which the fat frequency 33 is located.

Figure 7:
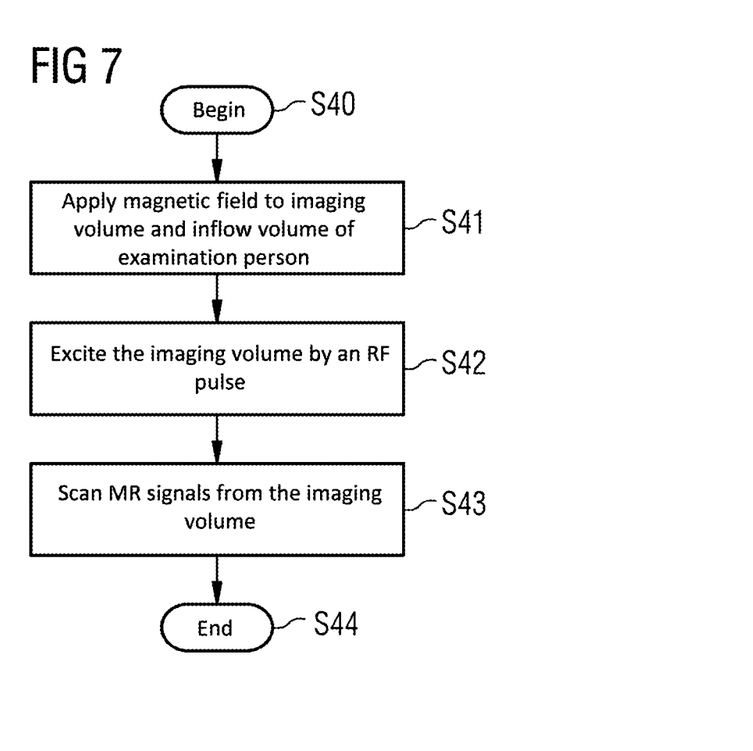
FIG. 7 is a flowchart of the basic steps for carrying out the method of vascular imaging according to an exemplary embodiment of the invention.

FIG. 7 is a flowchart of the basic steps for carrying out the method of vascular imaging according to an exemplary embodiment.

The method begins in step S40. In step S41, a magnetic field is applied to an imaging volume 30 and an inflow volume 31 of an examination person 12. In step S42, the imaging volume 30 is excited by an RF pulse 40, which fulfills a magnetization transfer function a fat saturation function, while the magnetic field is being applied. The RF pulse 40 has a frequency distribution whose frequencies are essentially higher than the center frequency of the water 32 in the imaging volume 30, and which comprises the fat frequency 33 in the imaging volume 30. The magnetic field has a magnetic field distribution, which has an apex with essentially no spatial gradient in the imaging volume 30 and a higher spatial gradient in the inflow volume 31. In step S43, MR signals from the imaging volume 30 are scanned in order to visualize vessels. The method ends in step S44.

To summarize, a method of vascular imaging with the use of a magnetic resonance system based on the TOF technique is provided, wherein a fixed magnetization in particular of brain tissue, spinal fluid and fat in an imaging volume 30, which generate undesirable background signals, inventively suppressed by an RF pulse 40 with simultaneously applied magnetic field. According to the invention, background signals are suppressed with the method of vascular imaging without affecting the spins of the vessel fluid flowing into the imaging volume. This enables faster and more efficient MR imaging for vascular imaging, which, due to low time and staff expenditure, has reduced examination costs.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for vascular imaging using a magnetic resonance (MR) apparatus comprising:
   using a computer to operate an MR data acquisition scanner, while an examination subject is situated therein, in order to apply a magnetic field to an imaging volume and to an inflow volume, from which liquid enters into the imaging volume of the examination subject;
   using said computer to operate said MR data acquisition scanner in order to radiate a radio-frequency (RF) pulse that excites nuclear spins in said imaging volume while the magnetic field is being applied;
   in said computer, generating control signals in order to radiate said RF pulse so as to fulfill a magnetization transfer function and a fat saturation function, giving said RF pulse a frequency distribution comprising frequencies that are higher than a center frequency of water in the imaging volume and said frequencies comprising the fat frequency in the imaging volume;
   in said computer, generating control signals in order to apply said magnetic field with a magnetic field distribution approximated by a function that has an apex with substantially no gradient in said imaging volume and that has a higher spatial gradient in said inflow volume;
   using said computer to operate said MR data acquisition scanner in order to acquire MR signals from the excited nuclear spins in the imaging volume that represent vessels in said imaging volume; and
   in said computer, transforming data represented by MR signals into image data and presenting said image data at a display screen in communication with said computer in order to visualize said vessels.

2. A method as claimed in claim 1 comprising generating said control signals in order to give said magnetic field said magnetic field distribution using, as said function that approximates said magnetic field distribution, a mathematical function of at least the second order.

3. A method as claimed in claim 1 wherein said imaging volume and said inflow volume are each formed as respective slices having a longitudinal axis oriented perpendicularly to said imaging volume and said inflow volume and wherein, along said longitudinal axis, a slice thickness of the inflow volume is equal to a multiple of a slice thickness of the imaging volume.

4. A method as claimed in claim 3 comprising generating said control signals to apply said magnetic field so as to give said apex of said function that approximates said magnetic field distribution a thickness that is equal to the slice thickness of the imaging volume.

5. A method as claimed in claim 1 comprising also implementing said method in an execution for at least one further imaging volume and at least one further inflow volume and, in said execution for said at least one further imaging volume and said at least one further inflow volume, adjusting the magnetic field distribution to said at least one further imaging volume and to said at least one further inflow volume by giving the magnetic field distribution said apex in said at least one further imaging volume and said higher spatial gradient in said at least one further inflow volume.

6. A method as claimed in claim 5 comprising applying said magnetic field in said execution of said method for said at least one further imaging volume and said at least one further inflow volume so as to give said magnetic field distribution a linear spatial shift of the magnetic field distribution.

7. A method as claimed in claim 5 comprising applying said magnetic field in said execution of said method for said at least one further imaging volume and said at least one further inflow volume so as to change a linear component of the magnetic field distribution.

8. A method as claimed in claim 5 wherein said imaging volume and said at least one further domain at least partially overlap and wherein said inflow volume and said at least one further inflow volume also at least partially overlap.

9. A method as claimed in claim 1 comprising using said computer to operate said MR data acquisition scanner in order to radiate said RF pulse by superimposing a first RF pulse and a second RF pulse.

10. A method as claimed in claim 9 wherein said first RF pulse has a first flip angle and wherein said second RF pulse has a second flip angle that is different from said first flip angle.

11. A method as claimed in claim 9 wherein said first RF pulse has a flip angle in a range between 20 and 90 degrees and a frequency substantially equal to said fat frequency in the imaging volume.

12. A method as claimed in claim 1 comprising using said computer to operate said MR data acquisition scanner to obtain a plurality of acquisitions of said MR signals from said imaging volume for each radiated RF pulse.

13. A method as claimed in claim 12 comprising using said computer to operate said MR data acquisition scanner to execute respective acquisitions in said plurality of acquisitions at regular time intervals.

14. A method as claimed in claim 12 comprising using said computer to operate said MR data acquisition scanner to execute acquisitions in said plurality of acquisitions in measurement groups with time intervals between individual acquisitions in each acquisition group, and by radiating an RF pulse between each acquisition group, with an average time interval between acquisitions being shorter than a predetermined threshold value.

15. A magnetic resonance (MR) apparatus comprising:
   an MR data acquisition scanner comprising a basic field magnet and a radio-frequency (RF) radiator;
   a computer configured to operate said MR data acquisition scanner, while an examination subject is situated therein, in order to apply a magnetic field with said basic field magnet to an imaging volume and to an inflow volume, from which liquid enters into the imaging volume of the examination subject;

said computer being configured to operate said MR data acquisition scanner in order to radiate a radio-frequency (RF) pulse from said RF radiator that excites nuclear spins in said imaging volume while the magnetic field is being applied;

said computer being configured to generate control signals to said Rf radiator in order to radiate said RF pulse so as to fulfill a magnetization transfer function and a fat saturation function, giving said RF pulse a frequency distribution comprising frequencies that are higher than a center frequency of water in the imaging volume and said frequencies comprising the fat frequency in the imaging volume;

said computer being configured to generate control signals to said basic filed magnet in order to apply said magnetic field with a magnetic field distribution approximated by a function that has an apex with substantially no gradient in said imaging volume and that has a higher spatial gradient in said inflow volume;

said computer being configured to operate said MR data acquisition scanner in order to acquire MR signals from the excited nuclear spins in the imaging volume that represent vessels in said imaging volume; and said computer being configured to transform data represented by MR signals into image data and to present said image data at a display screen in communication with said computer in order to visualize said vessels.

16. A non-transitory, computer-readable data storage medium encoded with programming instructions, said storage medium being loaded into a computer of a magnetic resonance (MR) apparatus that comprises an MR data acquisition scanner, said programming instructions causing said computer system to:

operate said MR data acquisition scanner, while an examination subject is situated therein, in order to apply a magnetic field to an imaging volume and to an inflow volume, from which liquid enters into the imaging volume of the examination subject;

operate said MR data acquisition scanner in order to radiate a radio-frequency (RF) pulse that excites nuclear spins in said imaging volume while the magnetic field is being applied;

generate control signals in order to radiate said RF pulse so as to fulfill a magnetization transfer function and a fat saturation function, giving said RF pulse a frequency distribution comprising frequencies that are higher than a center frequency of water in the imaging volume and said frequencies comprising the fat frequency in the imaging volume;

generate control signals in order to apply said magnetic field with a magnetic field distribution approximated by a function that has an apex with substantially no gradient in said imaging volume and that has a higher spatial gradient in said inflow volume;

operate said MR data acquisition scanner in order to acquire MR signals from the excited nuclear spins in the imaging volume that represent vessels in said imaging volume; and transform data represented by MR signals into image data and present said image data at a display screen in communication with said computer in order to visualize said vessels.

* * * * *